(12) United States Patent
Zhu et al.

(10) Patent No.: US 7,541,470 B2
(45) Date of Patent: Jun. 2, 2009

(54) PROCESSES FOR MAKING PIOGLITAZONE AND COMPOUNDS OF THE PROCESSES

(75) Inventors: Jie Zhu, Nijmegen (NL); Lambertus Thijs, Nijmegen (NL)

(73) Assignee: Synthon IP Inc., Gainesville, VA (US)

( * ) Notice: Subject to any disclaimer, the term of this patent is extended or adjusted under 35 U.S.C. 154(b) by 439 days.

(21) Appl. No.: 11/060,886

(22) Filed: Feb. 19, 2005

(65) Prior Publication Data

US 2007/0167629 A1    Jul. 19, 2007

Related U.S. Application Data

(60) Provisional application No. 60/545,857, filed on Feb. 20, 2004.

(51) Int. Cl.
  *C07D 417/12*    (2006.01)
(52) U.S. Cl. .................................. 546/269.7
(58) Field of Classification Search ............... 546/269.7
  See application file for complete search history.

(56) References Cited

U.S. PATENT DOCUMENTS

| 4,287,200 | A | 9/1981 | Kawamatsu et al. |
| 4,438,141 | A | 3/1984 | Kawamatsu et al. |
| 4,582,839 | A | 4/1986 | Meguro et al. |
| 4,687,777 | A | 8/1987 | Meguro et al. |
| 4,898,947 | A | 2/1990 | Meguro et al. |
| 5,965,584 | A | 10/1999 | Ikeda et al. |
| 5,965,589 | A | 10/1999 | Sohda et al. |
| 5,990,139 | A | 11/1999 | Yano et al. |
| 6,207,690 | B1 | 3/2001 | Urban et al. |
| 6,271,243 | B1 | 8/2001 | Ikeda et al. |
| 6,288,096 | B1 | 9/2001 | Andersson et al. |
| 2005/0054684 | A1 | 3/2005 | Zhu et al. |
| 2005/0059708 | A1 | 3/2005 | Pospisilik et al. |

FOREIGN PATENT DOCUMENTS

| EP | 0 008 203 A1 | 2/1980 |
| EP | 0 257 781 A1 | 7/1987 |
| EP | 0 283 035 A1 | 9/1988 |
| EP | 0 193 256 B1 | 4/1989 |
| EP | 0 506 273 B1 | 5/1995 |
| JP | 9-25273 | 1/1997 |
| WO | WO 02/088120 A1 | 11/2002 |

OTHER PUBLICATIONS

"Novel Benzoxazole 2,4-Thiazolidinediones as Potent Hypoglycemic Agents. Synthesis and Structure-Activity Relationships," Chem. Pharm. Bull. 45(12) pp. 1984-1993 (1997).
"Preparation of 3-Aromatic-substituted propionic acid or acrylic acid derivatives as antidiabetics", Kitajima et al., CA 134:41915 (2000).
"Preparation of (oxazolyl)alkoxyphenylpropionic acid derivatives as hypoglycemics and hypolipemics", Takeno et al., CA 126:89361 (1997).
"Hybridization of Non-Sulfonylurea Insulin Secretagogue and Thiazolidinedione-Derived Insulin Sensitizer", Kitajima et al., Bioorganic & Medicinal Chemistry Letters, 10(2000) 2453-2456.

*Primary Examiner*—Patricia L Morris
(74) *Attorney, Agent, or Firm*—Mark R. Buscher

(57) ABSTRACT

Pioglitazone can be made via a Darzens Condensation reaction in an industrially useful process.

17 Claims, No Drawings

PROCESSES FOR MAKING PIOGLITAZONE AND COMPOUNDS OF THE PROCESSES

This application claims the benefit of priority under 35 U.S.C. § 119(e) from U.S. Provisional Patent Application Ser. No. 60/545,857, filed Feb. 20, 2004, the entire contents of which are incorporated herein by reference.

BACKGROUND OF THE INVENTION

The present invention relates to processes of manufacturing pioglitazone, which is a thiazolidinedione derivative, and salts thereof such as pioglitazone hydrochloride, and to compounds useful in the processes.

Some thiazolidinedione derivatives exhibit hypoglycemic activity and/or blood lipid lowering activity. They have been proposed for use in treating, inter alia, diabetes. Some of the well known and/or studied thiazolidinediones include pioglitazone, troglitazone, and rosiglitazone.

Pioglitazone, which is chemically 5-[[4-[2-(5-ethyl-2-pyridyl)-ethoxy]phenyl]methyl]-2,4-thiazolidinedione and corresponds to the formula (1)

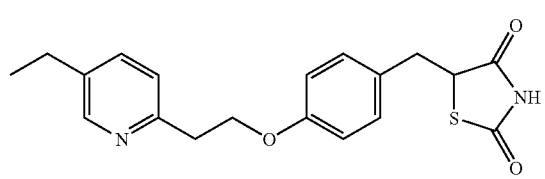

(1)

is a commercially approved antidiabetic agent. Pharmaceutical compositions comprising pioglitazone, as the hydrochloride salt, are marketed under the brand name ACTOS® (Takeda Chemical Ind.) for treatment of type II diabetes.

Pioglitazone and its hydrochloride have been disclosed in EP 193256 and corresponding U.S. Pat. No. 4,687,777. In these patents, the thiazolidinediones, such as pioglitazone, can be formed by cyclizing an alpha-bromo acid ester (2) with thiourea. The resulting imino-thiazolidinone (3) is then hydrolyzed to make the corresponding glitazone. For pioglitazone, the reaction can be represented as follows:

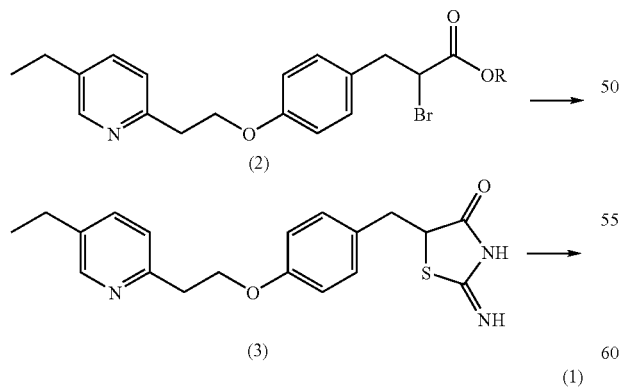

The starting alpha-bromo acid ester (2) is taught to be prepared by Meerwein arylation. This process comprises preparing the corresponding aniline (4), diazotation thereof in the presence of hydrobromic acid, and coupling of the product of diazotation with an acrylic acid ester (5) under catalysis by cuprous oxide as shown on the scheme below:

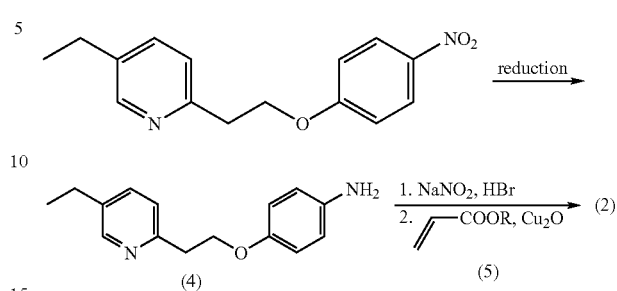

However, forming the alpha-bromo acid ester by the Meerwein arylation reaction can be problematic. The sequence of reactions within this transformation must be controlled precisely. Otherwise the diazo-compound generated during the reaction can react with another nucleophile such as the bromide anion leading to a complicated outcome. Therefore, the reaction often gives a complicated result and lower chemical yield. Furthermore, acrylate esters (5) are toxic and irritating compounds.

Japanese published patent application 09-25273 deals with an improved method for making benzyl-thiazolidinones of a general formula (A)

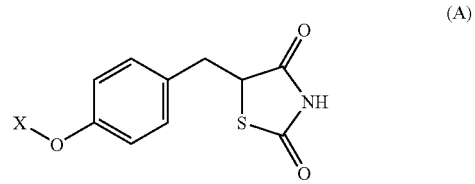

(A)

from a phenyl lactate derivative (B)

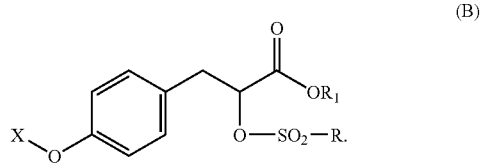

(B)

The starting material (B) is taught to be prepared from the corresponding phenyl lactic acid by esterification and sulfonation. Schematically this can represented as follows:

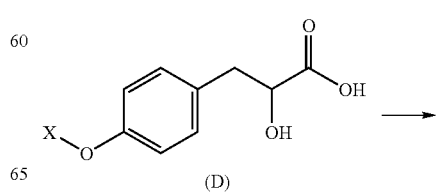

-continued

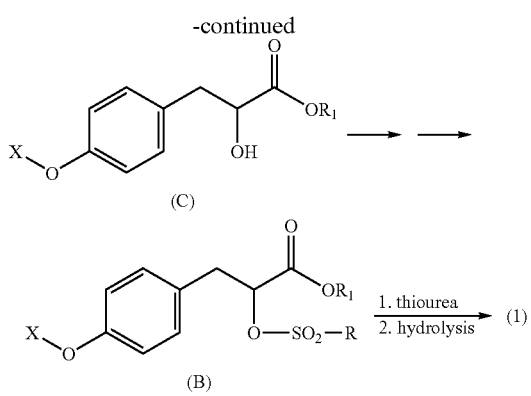

However no method is given for making the starting phenyl lactic acid (D). Instead, the phenyl lactic acids exemplified in JP 09-25273, which include compounds where "X" is a pyridyl-containing moiety, are believed to be commercially available. While some phenyl lactic acids are commercially available, a phenyl lactic acid derivative needed to make pioglitazone, i.e. compound (D) where X is 5-ethyl-2-pyridylethyl group, is not known to be commercially available.

It would be desirable to find alternative processes for making thiazolidinediones such as pioglitazone. It would further be desirable to find an improved process for making pioglitazone from inexpensive and/or relatively easy to manufacture starting compounds without the need of a diazotation reaction.

SUMMARY OF THE INVENTION

The present invention is based on the discovery of a process for making pioglitazone through the use of a Darzens Condensation reaction, e.g. glycidic acid condensation. Such a process can avoid working with the phenyl lactic acid (D) and does not require the performance of a diazotation.

Accordingly a first aspect of the invention relates to a process for making pioglitazone which comprises carrying out a Darzens Condensation reaction. The "Darzens Condensation" reaction as used herein means a chemical reaction comprising formation of α,β-epoxyesters (glycidic esters) by the condensation of an aldehyde with an ester of an α-haloacid. Thus, pioglitazone can be made by a process which comprises employing as a step (i.e. "via") a Darzens Condensation reaction between an aromatic aldehyde and an ester of a haloacetic acid in the presence of a base. In particular, a novel intermediate compound of formula (7)

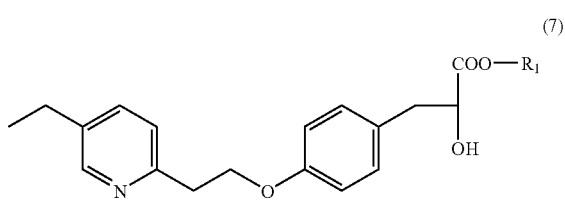

wherein $R_1$ is $C_1$-$C_4$ alkyl group, can be formed via a Darzens Condensation reaction and then converted to pioglitazone. A variety of synthetic routes and starting materials can be used to form the compound of formula (7), each of them using a Darzens Condensation reaction, and several are described more fully hereinafter.

Another aspect of the invention relates to a conversion of the compound of formula (7) into pioglitazone, which comprises:

reacting a sulfonylchloride of the formula R—SO$_2$Cl with a compound of formula (7)

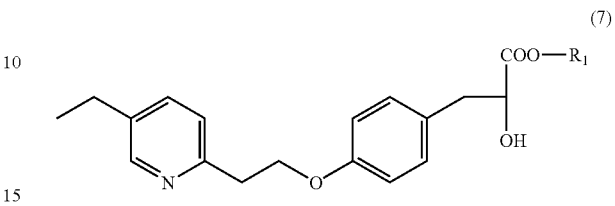

wherein R represents a $C_1$-$C_4$ alkyl group or an optionally substituted phenyl group and $R_1$ represents a $C_1$-$C_4$ alkyl group, to form a compound of formula (8)

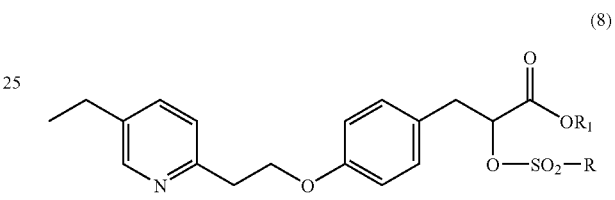

wherein R and $R_1$ are as defined above;

reacting the compound of formula (8) with thiourea to form the compound of formula (3):

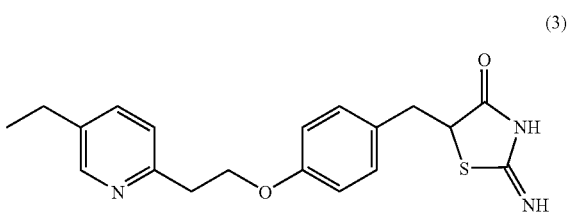

and hydrolyzing the compound of formula (3) to form pioglitazone of formula (1):

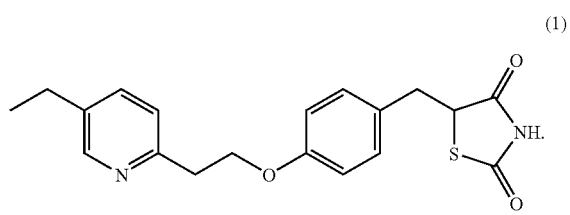

In the context of the present invention, pioglitazone of formula (1) includes pioglitazone per se as well as all salts thereof such as pioglitazone hydrochloride. Though not required, the compound of formula (7) is preferably formed via a Darzens Condensation reaction as noted above.

An additional aspect of the present invention relates to various intermediates that are useful in the processes of mak ing pioglitazone via a Darzens Condensation reaction; specifically to a compound selected from the formula (7), (8), and (15).

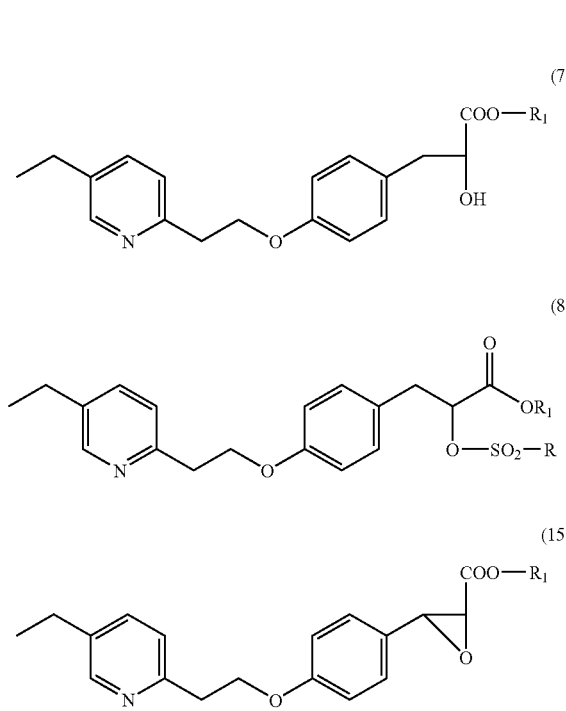

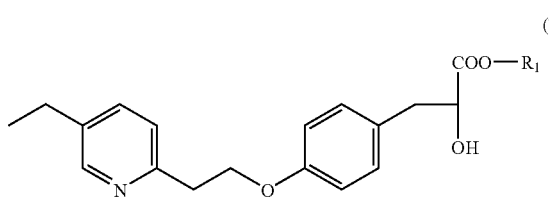

wherein R represents a $C_1$-$C_4$ alkyl group or an optionally substituted phenyl group and $R_1$ is $C_1$-$C_4$ alkyl group.

DESCRIPTION OF THE INVENTION

The present invention relates to the discovery of a new key intermediate in making pioglitazone, namely a compound of formula (7), and to the discovery that such a compound can be effectively made by a Darzens Condensation reaction:

wherein $R_1$ represents a $C_1$-$C_4$ alkyl group. By using a Darzens Condensation reaction both the disadvantages of the Meerwein reaction and the need to make an appropriate phenyl lactic acid of formula (D) are avoided. Further the compound of formula (7) is easily converted to pioglitazone. Thus, pioglitazone can be made from inexpensive starting materials by a convenient and high yield process which is easy to scale up to produce pioglitazone reliably in a commercial scale.

The compound of formula (7) can advantageously be prepared via a Darzens Condensation reaction. Three embodiments using a Darzens Condensation are described below.

The first process is outlined in Scheme 1:

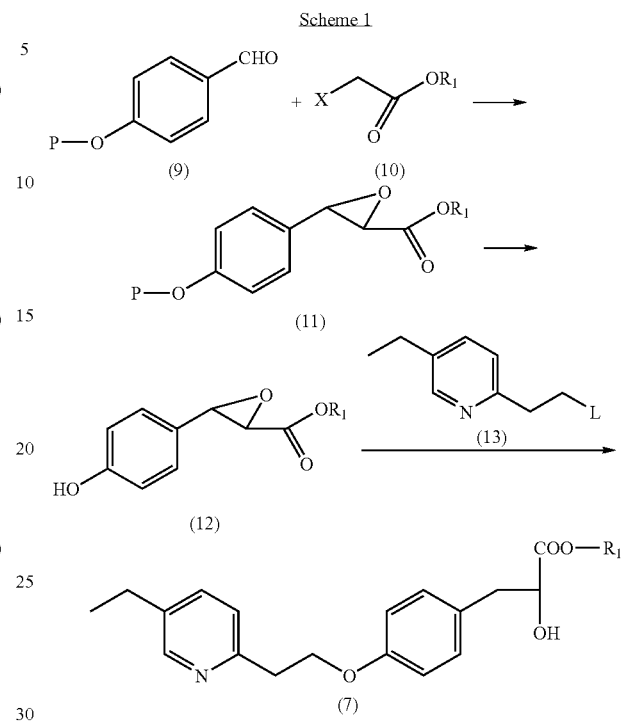

In the above formulas, the variables are as follows:
$R_1$ represents a $C_1$-$C_4$ alkyl group, including branched $C_3$-$C_4$ chain, and preferably is methyl, ethyl, isopropyl or tertiary-butyl;

X represents a halogen such as chlorine or bromine, preferably chlorine;

P represents a reducible hydroxy-protective group, for instance a benzyl group

L is a leaving group such as a halogen, methanesulfonyloxy-, or p-toluenesulfonyloxy-group.

The starting benzaldehydes (9) are commercially available or may be made according to methods well known in the art. The ethylpyridine compound (13) may be prepared according to known methods, e.g., by the methods analogous to those shown in EP 506273. Typically compound (13) is 2-(5-ethylpyridynyl )ethyl methanesulfonate.

In the first step, the p-hydroxybenzaldehyde, having the OH-group protected by a reducible protective group (i.e. a group which is removable under reductive conditions), for instance the p-benzyloxybenzaldehyde, is subjected to a Darzens Condensation reaction with a haloacetate. The Darzens Condensation reaction involves coupling both components in a solvent, for instance in an alcoholic solvent, in the presence of a base. A preferred alcoholic solvent should have the same alkyl group as is the $R_1$ alkyl group in the haloacetate; i.e. the solvent should have the formula $R_1OH$. The preferred base is an alcoholate, especially one having the same alkyl group $R_1$ as the haloacetate; i.e. the alcoholate should the formula $R_1O^-M^+$ where M represents an alkali metal such as sodium or potassium. By using the same alkyl moiety, the risk of transesterification side-reactions can be reduced. Thus, when coupling the above p-benzyloxybenzaldehyde with a tertiary-butyl haloacetate (for instance tertiary-butyl chloroacetate), the solvent would preferably be tertiary-butyl alcohol and the base would preferably be a tertiary-butoxide, for instance potassium tertiary-butoxide. The reaction may proceed at temperatures close to ambient and generally proceeds very smoothly and with a high yield.

The product of the Darzens reaction is a glycidic ester. In this embodiment the glycidic ester is represented by the formula (11). It may be, if needed, isolated from the reaction mixture, preferably after conventional purification of the reaction mixture, by precipitation or by evaporation of the solvent. The Darzens reaction produces the glycidic ester (11) as a mixture of cis- and trans isomers. Both isomers are equally suitable for the next reaction. Yields of the reaction may exceed 80%.

The second step involves the reduction of the compound (11), within which the protective group P is removed and the oxiran ring in the glycidic ester is opened to produce the di-hydroxy compound of formula (12). Such a conversion to the compound (12) can be carried out in one or more steps. Preferably, the reductive conditions are selected in such a way that both reactions proceed in one step. However, it is also possible that the protective group is removed first and then the oxiran ring is opened, or vice versa. In such cases, the corresponding intermediate product may also be isolated.

For the one-pot reduction, the conditions of catalytic hydrogenolysis are suitable, i.e. the glycidic ester is subjected, in an inert solvent, to an action of hydrogen gas under catalysis of a suitable hydrogenation catalyst, for instance palladium on carbon. Suitable solvents comprise, for instance, an ether such as tetrahydrofuran, an alcohol such as methanol or an ester such as ethyl acetate. The hydrogen gas may be introduced under normal pressure, but advantageously under enhanced pressure in a closed vessel. After removal of the catalyst, the formed dihydroxy-compound (12) may be, if desired, obtained in an isolated form, for instance by precipitation or by evaporation the solvent. Yield of the reaction may be higher than 90%.

Alternatively hydrides can be used as hydrogenolytic agents.

In the next step, the dihydroxy compound (12) is coupled with a 5-ethyl pyridine ethanol compound substituted by a suitable leaving group (compound (13)) within an ether-forming reaction, under the presence of a base. Usually the solvent is an organic aprotic solvent, for instance dimethylsulfoxide or acetonitrile, and the base is typically an inorganic hydroxide, inorganic carbonate, or quaternary ammonium hydroxide, for instance potassium carbonate. The alkylation reaction can be carried out by adding the compound of formula (13), such as 2-ethylpyridin-5yl-ethyl mesylate or tosylate, either per se, or in the same, or in a different solvent, to the mixture of the hydroxyester and the base in the solvent. Optionally, an additional portion of the same or a different base can be added to the solution during the process. The alkylation reaction preferably proceeds at elevated temperatures.

This ether-forming reaction can be accompanied by an unwanted elimination reaction under formation of a vinyl pyridine side-product. In this respect, selecting proper reaction conditions including the solvent, reaction temperature and time, and the kind and amount of the base, can serve to minimize the elimination. Suitable reaction conditions include refluxing both components in acetonitrile in the presence of potassium carbonate for several hours. Additional suitable conditions can be determined using routine experimentation and ordinary skill based on the desired preferences.

Unreacted dihydroxy-compound, if any, may be completely recovered during the work-up the reaction mixture by washing with a base and neutralization of the washings.

A second embodiment of a Darzens Condensation reaction for making a compound of formula (7) is depicted in the Scheme 2 below.

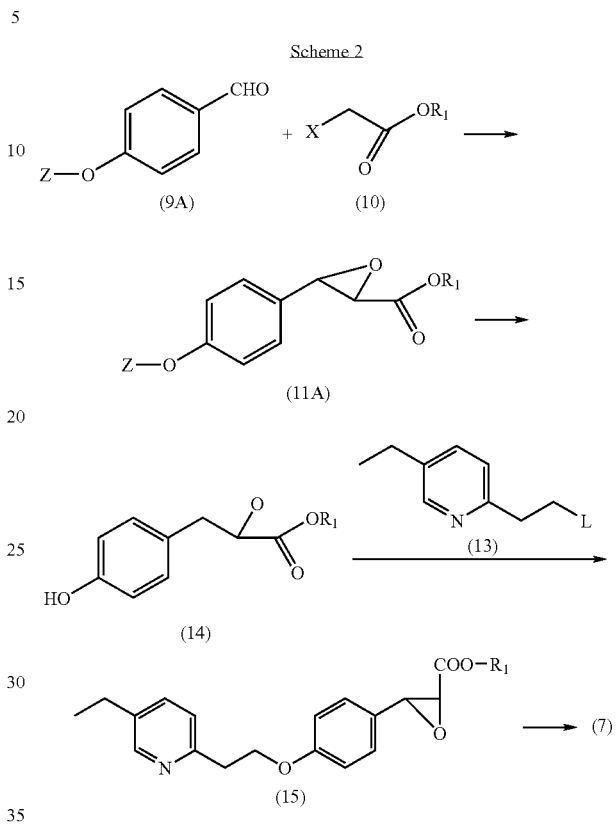

The starting material is a p-hydroxybenzaldehyde (9A) having the OH-group protected by a hydrolyzable protective group Z. Such a group can be removed when desired by a hydrolysis reaction. Examples of such protective groups are tetrahydropyranyl and trityl group.

Compounds (9A) are either commercially available or can be prepared by conventional methods.

The compound (9A) is subjected to the Darzens Condensation reaction with a haloacetate, under essentially same conditions as disclosed above.

The product (11A) is then subjected to a removal of the hydrolyzable protective group. The removal is accomplished by treating the compound in a suitable solvent with an acid such as hydrochloric acid, trifluoroacetic acid, or methane sulfonic acid. As a result, p-hydroxyphenyl glycidate (14) is formed. The compound (14) may be isolated, if desired, from the neutralized reaction mixture by extraction into an organic solvent and evaporation of the solvent.

The p-hydroxyphenyl glycidate is subjected to an ether-forming reaction with the ethylpyridine derivative (13), basically under conditions disclosed above.

In the last step, the so formed compound (15) is converted to the compound (7) under conditions that will be discussed below.

The third embodiment of a Darzens Condensation reaction for making a compound of formula (7) is depicted in Scheme 3.

Scheme 3.

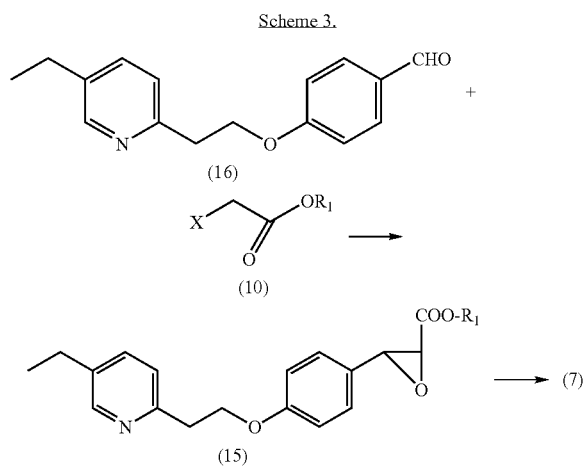

In the first step, the compound (16) reacts with the halo acetate (10) under conditions of a Darzens Condensation reaction, essentially as described above. The pyridyl-substituted aldehyde compound (16) may be made according to the process disclosed in EP 257781. In a suitable variant of the process disclosed therein, acetonitrile is used as a solvent and the crude product is used in the further synthesis without an isolation step. The product is the pyridyl substituted glycidic ester of the formula (15), i.e. the same product as obtained by the above second embodiment method. It may be isolated from the reaction mixture after neutralization of the reaction mixture and removal of inorganic side products, by conventional isolation methods. The compound (15) is provided as a mixture of cis- and trans-isomers, both isomers being equally suitable for the next step.

The compound of formula (15) is converted to the desired compound (7) by a reaction involving opening the oxirane ring under formation of an OH-group. A suitable reaction is a hydrogenolysis, e.g. by catalytic hydrogenation or by action of hydrides. Catalytic hydrogenation, i.e. treatment of the compound (15) in an inert solvent with a hydrogen gas under presence of a catalyst, is preferred. In general, the reaction proceeds smoothly at ambient pressure of hydrogen, however, enhanced pressure may be used as well. The suitable catalyst is palladium on an inert support, for instance on charcoal.

After the reaction is complete (which can be simply monitored by conventional chromatographic methods), the catalyst is removed by filtration and the product may be isolated by evaporation of the solvent and purified if necessary.

By any of the above processes, the compound (7) may be obtained in a substantially pure and/or isolated form by purification of the reaction mixture prior to isolation and/or by isolation from the reaction mixture by conventional techniques/methods. After isolation, it may still be purified to the desired degree of purity by suitable means, e.g., by extraction of impurities, by chromatography, etc. Alternatively, it may be used in the next step without isolation.

The compound (7), however obtained, including by the phenyl lactic acid route, can be converted to pioglitazone by the following sequence of reactions depicted in Scheme 4.

Scheme 4

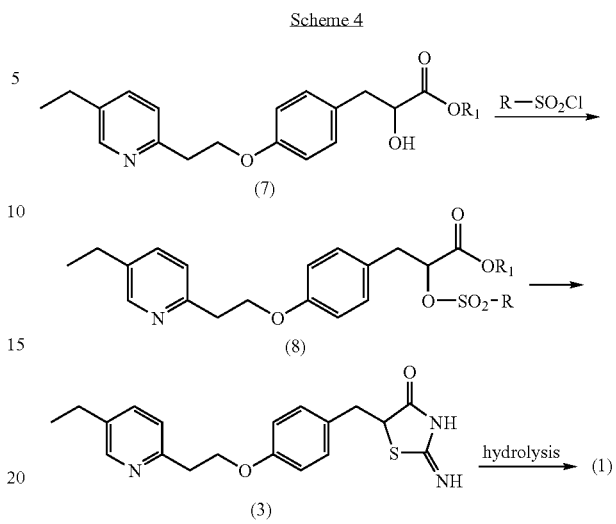

In the first step, the compound (7) reacts with an alkyl- or aryl-sulfonylchloride of the formula R—SO$_2$Cl in an inert solvent and in the presence of base to yield the compound of formula (8). R is a lower alkyl group ($C_1$-$C_4$) or an optionally substituted phenyl group. Typically R is methyl or p-tolyl. A suitable sulfonyl halide is methanesulfonyl chloride. A suitable base in the reaction is a tertiary amine, for instance triethyl amine or pyridine. A suitable solvent is any inert organic solvent, for instance toluene or dichloromethane. The reaction generally proceeds very smoothly at a temperature close to ambient and complete conversion may be obtained within several hours. Typically, the compound (7) reacts, in a toluene solvent, with a molar equivalent or a gentle molar excess of methane sulfonylchloride in the presence of the corresponding molar amount of the amine at 0-20° C. After the reaction is complete (the degree of conversion may be monitored by TLC or HPLC), the product may be preferably recovered from the reaction mixture after filtration and removal of the solvent.

In the second step, the compound (8), optionally after isolation from its reaction medium, is reacted with thiourea under analogous conditions as taught in JP 09-25273. Typically the reaction comprises refluxing the reagents in an alcoholic solvent in the presence of sodium acetate or other suitable weak base. The sulfur atom of thiourea replaces the —SO$_2$R group and the carboxyl group reacts with the amino group of thiourea. As a result, an iminothiazolidinone ring is formed to obtain the compound of formula (3). The conversion of the reaction may be monitored by a suitable method, for instance by TLC or HPLC. The product (3) is a solid and may be isolated as a precipitate after cooling the reaction mixture, diluting with water and neutralization.

In the last step, the imino-thiazolidinone (3) is converted to pioglitazone by an acidic hydrolysis that is known in the art.

The pioglitazone formed by whatever conversion route employing the key intermediate (7) of the present invention can be isolated and/or converted to a base or an acid addition salt, such as a pharmaceutically acceptable acid addition salt. Examples of such salts are pioglitazone hydrochloride, hydrobromide, maleate, fumarate, tartrate, citrate, malate, benzoate, mesylate, and tosylate.

Pioglitazone and its pharmaceutically acceptable salts are valuable pharmaceutical products. It may be used in various pharmaceutical compositions comprising pioglitazone and a pharmaceutically acceptable carrier or diluent. The compositions may be formulated for oral administration. The unit dosage forms include tablets and capsules. The pharmaceutical compositions and final forms comprising pioglitazone may be made by any known process. The tablet compositions may be formulated by known methods of admixture such as blending, filling, and compressing, by means of wet granulation, dry granulation, or direct compression.

Individual unit dose compositions comprising pioglitazone such as tablets or capsules may contain from 1 to 100 mg or 2 to 50 mg of the compound, such as an amount of 2.5, 5, 10, 15, 20, 30, or 45 mg of pioglitazone. Such a composition is normally taken from 1 to 3 times daily, such as once a day. In practice, the physician will determine the actual dosage and administration regimen, which will be the most suitable for the individual patient.

The pioglitazone may be used in the management of various types of hyperglycemia and diabetes, especially Type II diabetes. The present invention also includes the use of pioglitazone of the invention in the manufacture of a medicament for treating and/or preventing any one or more of these disorders. Pioglitazone compositions may be used in medical applications, e.g., in a treatment of certain forms of diabetes, either alone or in combination with other antidiabetic agents, for instance with metformin. The combination may be in a form of a single combination preparation, or by separate administration of drugs containing the above agents.

The present invention will be further illustrated by way of the following non-limiting examples.

Preparation 1: The compound of formula (16)

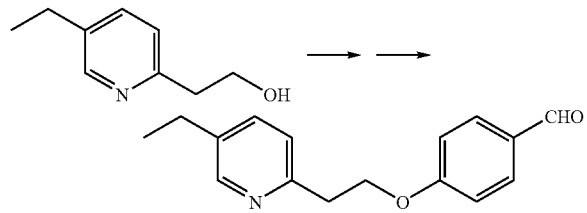

To a solution of 5-ethyl pyridyl ethanol (16.67 g) in toluene (100 ml), triethylamine (11.67 g) was added with stirring and cooling (ice water) followed by a slower (in 20 minutes) addition of a solution of methane sulphonyl chloride (13.25 g). After completion, the mixture was further stirred for 30 minutes at the temperature water (50 ml) was added and it was stirred for 20 minutes. Separated water layer was extracted with ethyl acetate (150 ml). Combined organic layer was dried over $Na_2SO_4$ and concentrated in vacuo to give an oily product (27.2 g).

A mixture of above compound (27.2 g), p-hydroxybenzaldehyde (14.76 g) and potassium carbonate (16.70 g) in acetonitrile (300 ml) was refluxed, with stirring, for 7 hours. After cooling down to room temperature, water (100 ml) was added to dissolve the solid. Mixture was concentrated to get rid of acetonitrile and re-dissolved in ethyl acetate (400 ml). The solution was washed with NaOH (1M, 2×25 ml), water (25 ml), HCl (0.2 M, 25 ml) and brine (25 ml). After drying over $Na_2SO_4$, concentration in vacuo gave an oily product (24.1 g).

EXAMPLE 1

29.4 g of potassium tert. butoxide was dissolved in 440 ml of tert. butyl alcohol and the solution was added dropwise during 4.5 hour to a stirred mixture of 50 g of 4-benzyloxybenzaldehyde and 42.4. g of tert.butyl chloroacetate. After the addition was complete, the mixture was filtered through celite and the solution was concentrated giving an oil that crystallized after a storage in a cold room. Yield 67.75 g of a white solid (compound (11), t-butyl 3-(4-benzyloxy)-phenyl-2,3-epoxypropanoate).

63 g of the compound (11) was dissolved in 1500 ml of ethyl acetate and 5 g of wetted 10% palladium/carbon catalyst were carefully added. The mixture was saturated by hydrogen gas and stirred under hydrogen atmosphere overnight. The mixture was filtered through celite, the filter was washed with 250 ml of ethyl acetate and the solvent was evaporated to give 42.3 g of a white solid (compound (12), t-butyl 3-(4-hydroxyphenyl)-2-hydroxypropanoate)

15 g of the compound (12) and 19.2 g of potassium carbonate were charged into 400 ml of acetonitrile and the mixture was stirred at 60° C. for 30 minutes. Then, 17.3 g of 5-ethylpyridine-2-ethyl mesylate dissolved in 50 ml of acetonitrile was added dropwise within 30 minutes. The reaction mixture was refluxed for 7 hours. Then the mixture was cooled down and allowed to stay overnight. Then 50 ml of water was added and most of the solvent was evaporated in vacuo. To the rest, 500 ml of ethyl acetate was added. The mixture consisted of two layers. The organic layer was separated, washed with 4×50 ml of 2M aqueous sodium hydroxide and 2×25 ml of brine, dried and concentrated to yield 16 g of an oily product (compound (7), tert. butyl 3-(4-(5-ethyl-2-pyridyl)ethyloxy)phenyl-2-hydroxypropanoate). The aqueous layer was neutralized with 15 ml of conc. HCl and extracted with 300 ml of ethyl acetate. The organic layer was separated, dried and concentrated to yield 6.8 g of the recovered starting diol.

16 g of the compound (7) was dissolved in 100 ml of toluene, the solution was cooled down to 5° C., 4.2 g of triethylamine was added, followed by a solution of 4 g of methane sulfonylchloride in 20 ml of toluene. The addition of the toluene solution was done slowly, without allowing the solution to warm up to more than 5° C. After the addition was finished, the reaction mixture was stirred for 30 minutes. 250 ml ethyl acetate and 50 ml water were added and stirred. Separated organic layer was washed with 2×25 ml of brine and dried. The solvent was evaporated, yielding 18.7 g of an oil (compound (8), tert. butyl 3-(4-(5-ethyl-2-pyridyl)ethyloxy)phenyl-2-mesyloxypropanoate).

7 g of the compound (8) was dissolved in 60 ml of ethanol and 1.6 g of thiourea and 3.2 g of sodium acetate were added under stirring. The mixture was brought to reflux and stirred for 8 hours. After cooling, 25 ml of water was added. The solution was concentrated to approx. half of the volume, 100 ml of water was added and the mixture was stirred for 45 minutes. The precipitated solid was filtered off and washed with 50 ml of ether. After drying, 2.32 g of a white solid was obtained (compound (3), 5-[[4-[2-(5-ethyl-2-pyridyl)-ethoxy]phenyl]methyl]-thiazolidin-4-one-2-imine.

1.7 g of the compound (3) was dissolved in 60 ml of 1M HCl, the mixture was brought to reflux and stirred for 9 hours. The mixture was cooled down and 35 ml of 2N aqueous NaOH was added. The precipitated solid was filtered, washed with 20 ml of water and 20 ml of methanol. After drying, 1.45 g of pioglitazone was obtained.

EXAMPLE 2

To a solution of 24 g of the pyridylaldehyde (16) and 13.48 g of ethyl chloroacetate in 150 ml ethanol, 9.52 g of sodium ethoxide was added in parts under stirring and cooling with ice water. After stirring at room temperature for 3 hours, the mixture was neutralized with 6N HCl. The solid was filtered off and washed with ethanol. The filtrate was concentrated and re-dissolved in 300 ml ethyl acetate. The organic solution was washed with 2×25 ml of water, 25 ml of brine, dried over anhydrous sodium sulfate and concentrated to give an oily product (approx. 31 g, compound of formula (15), ethyl 3-(4-(5-ethyl-2-pyridyl)ethyloxy)phenyl-2,3-epoxypropanoate).

A mixture of the 26 g of the compound (15) and 1.3 g of 10% palladium/carbon catalyst in 400 ml methanol was saturated with hydrogen gas and was stirred in hydrogen atmosphere at normal pressure and room temperature for 18 hours. The catalyst was filtered off and washed with methanol. The filtrate was concentrated in vacuo to give an oily product (approx. 25.5. g, compound (7), ethyl 3-(4-(5-ethyl-2-pyridyl)ethyloxy)phenyl-2-hydroxypropanoate).

To a solution of 25.5 g of the compound (7) in 150 ml of toluene, 8.6 g of triethylamine was added under stirring and cooling with ice water. Then 9.73 g of methane sulfonylchloride was added within approx. 5 minutes. The reaction mixture was further stirred at approx. 5° C. for 30 minutes. 250 ml of ethyl acetate was added, followed by 100 ml of water. After stirring for 20 minutes, layers were allowed to separate and the separated organic layer was washed with 2×25 ml of water, 25 ml of brine and dried over anhydrous sodium sulfate. The solution was concentrated in vacuo to give an oily product (31 g, compound (8), ethyl 3-(4-(5-ethyl-2-pyridyl)ethyloxy)phenyl-2-mesyloxypropanoate).

A mixture of 31.0 g of the compound (8), 6.38 g of thiourea and 6.89 g of sodium acetate in 200 ml of ethanol was refluxed for 8 hours under stirring. Then the mixture was cooled to room temperature and 30 ml of water was added. The mixture was concentrated to get rid most of the ethanol. 100 ml of water was added to the mixture under good stirring and the mixture was stirred for 30 minutes. The solid product was collected by filtration and washed with 3×25 ml of ethyl acetate. The ethyl acetate layer from the filtrate was concentrated and re-dissolved in 30 ml of ethyl acetate. The mixture was stirred for 30 minutes and the second crop of a solid product was collected by filtration and washing with 2×10 ml of the ethyl acetate. Yield: 9.9 g+1.65 g (compound (3)).

A mixture of 11.55 g of compound (3) in 100 ml of 2N HCl was refluxed under stirring for 4.5 hours. Then the mixture was cooled to room temperature and neutralized to pH about 7. The solid was collected by filtration and washed with 2×25 ml of ethanol. After drying, 11.1 g of pioglitazone was obtained.

All of the patents mentioned above are expressly incorporated herein in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

What is claimed is:

1. In a process for making pioglitazone, the improvement for which comprises forming a compound of formula (7) via a Darzens Condensation reaction

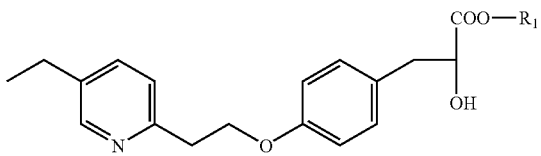

wherein $R_1$ is $C_1$-$C_4$ alkyl group, and converting said compound of formula (7) to pioglitazone.

2. A process for making pioglitazone, which comprises: reacting a sulfonylchloride of the formula R—SO$_2$Cl with a compound of formula (7)

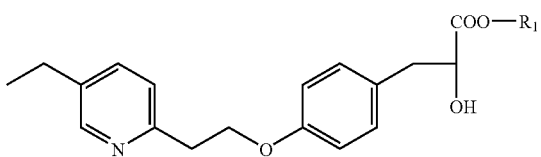

wherein R represents a $C_1$-$C_4$ alkyl group or an optionally methyl-substituted phenyl group and $R_1$ represents a $C_1$-$C_4$ alkyl group, to form a compound of formula (8)

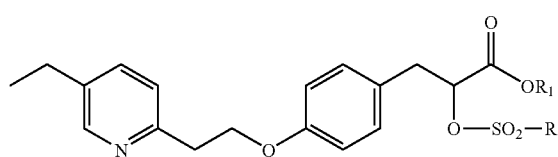

wherein R and $R_1$ are as defined above;
reacting said compound of formula (8) with thiourea to form the compound of formula (3):

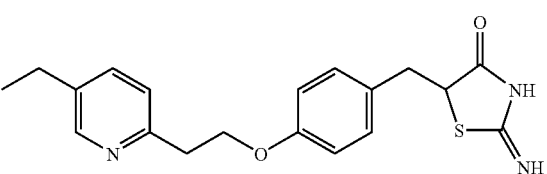

and hydrolyzing said compound of formula (3) to form pioglitazone of formula (1):

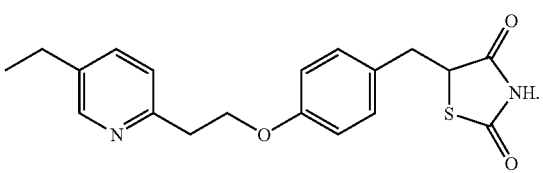

3. The process according to claim 2, which further comprises forming said compound of formula (7) via a Darzens Condensation reaction.

4. The process according to claim 3, wherein said formation of said compound of formula (7) comprises:

reacting a benzaldehyde of formula (9)

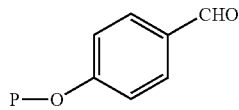
(9)

wherein P is a reducible hydroxy-protecting group, with a haloacetate of formula (10)

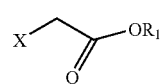
(10)

wherein X is a halogen and $R_1$ is as previously defined, in an alcoholic solvent and in the presence of a base to form a glycidic ester of formula (11)

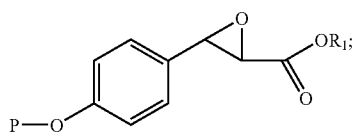
(11)

converting, in one or more steps, said compound of formula (11) into a dihydroxy compound of formula (12)

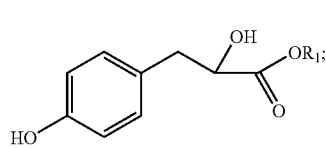
(12)

coupling said compound of formula (12) with an ethylpyridine compound of formula (13)

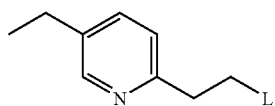
(13)

wherein L is a leaving group, to form said compound of formula (7); and optionally isolating said compound of formula (7) before reacting it with said sulfonylchloride compound.

5. The process according to claim 4, wherein $R_1$ is ethyl or tert-butyl, P is a benzyl group, and L is selected from the group consisting of halogen, methanesulfonyloxy-group, and toluenesulfonyloxy-group.

6. The process according to claim 4, wherein said alcoholic solvent is $R_1OH$ and said base is an alcoholate of the formula $R_1O^-M^+$ wherein M is an alkali metal, and $R_1$ is the same in said solvent, said alcoholate and said haloacetate of formula (10).

7. The process according to claim 6, wherein X is chloro or bromo land M is sodium or potassium.

8. The process according to claim 3, wherein said formation of said compound of formula (7) comprises:

reacting a benzaldehyde compound of formula (9A)

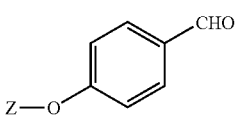
(9A)

wherein Z is a hydrolysable protective group, with a haloacetate of formula (10)

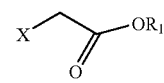
(10)

wherein X is a halogen and $R_1$ is as previously defined, in an alcoholic solvent and in the presence of a base to form a glycidic ester of formula (11A)

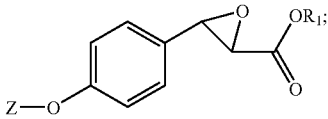
(11A)

deprotecting said compound of formula (11A) to form a compound of formula (14)

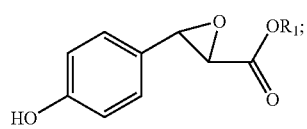
(14)

coupling said compound of formula (14) with an ethylpyridine compound of formula (13)

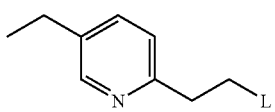
(13)

wherein L is a leaving group, to form a compound of formula (15)

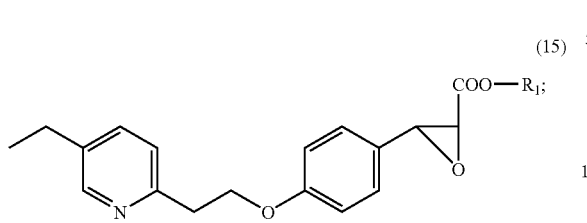

converting said compound of formula (15) to said compound of formula (7); and optionally isolating said compound of formula (7) before reacting it with said sulfonylchloride compound.

9. The process according to claim 8, wherein $R_1$ is ethyl or tertiary-butyl, Z is a tetrahydropyranyl or trityl group, and L is selected from the group consisting of halogen, methanesulfonyloxy-group, and toluenesulfonyloxy-group.

10. The process according to claim 8, wherein said alcoholic solvent is $R_1OH$ and said base is an alcoholate of the formula $R_1O^-M^+$ wherein M is an alkali metal, and $R_1$ is the same in said solvent, said alcoholate and said haloacetate of formula (10).

11. The process according to claim 10, wherein X is chloro or bromo and M is sodium or potassium.

12. The process according to claim 3, wherein said formation of said compound of formula (7) comprises:

reacting a benzaldehyde of formula (16)

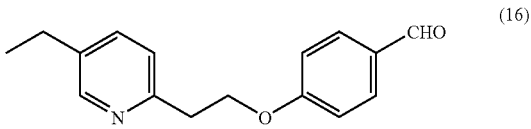

with a haloacetate of formula (10)

wherein X is a halogen and $R_1$ is as previously defined, in an alcoholic solvent and in the presence of a base to form a glycidic ester of formula (15)

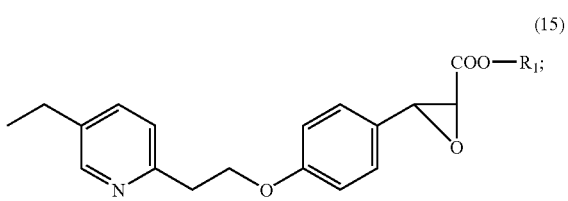

converting said compound of formula (15) to said compound of formula (7); and optionally isolating said compound of formula (7) before reacting it with said sulfonylchloride compound.

13. The process according to claim 12, wherein $R_1$ is ethyl or tertiary-butyl.

14. The process according to claim 12, wherein said alcoholic solvent is $R_1OH$ and said base is an alcoholate of the formula $R_1O^-M^+$ wherein M is an alkali metal and $R_1$ is the same in said solvent said alcoholate and said haloacetate of formula (10).

15. The process according to claim 6, wherein X is chloro or bromo and M is sodium or potassium.

16. The process according to claim 2, wherein R represents a methyl group.

17. The process according to claim 2, wherein R represents a p-tolyl group.

* * * * *